United States Patent
Sagehashi

(10) Patent No.: US 6,285,693 B1
(45) Date of Patent: Sep. 4, 2001

(54) LASER APPARATUS

(75) Inventor: Hideo Sagehashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/351,295

(22) Filed: Jul. 12, 1999

(30) Foreign Application Priority Data

Jul. 13, 1998 (JP) .................................................. 10-197862

(51) Int. Cl.$^7$ .............................. H01S 3/121; H01S 3/00
(52) U.S. Cl. .......................................... 372/38.03; 372/14
(58) Field of Search .................................. 372/38.03, 14, 372/38; 194/229, 230, 293

(56) References Cited

U.S. PATENT DOCUMENTS 6,008,466  *  12/1999  Hosoda .......................... 219/121.62

* cited by examiner

Primary Examiner—Frank G. Font
Assistant Examiner—Armando Rodriguez
(74) Attorney, Agent, or Firm—Foley & Lardner

(57) ABSTRACT

A laser apparatus which is capable of terminating a irradiating operation using a laser beam without fail by opening switches even if a component of an irradiation switch unit have trouble during the irradiating operation in a continuous irradiation mode. A first switch (11) and a second switch (12) are connected electrically in series by signal lines (18) and are disposed in a side-by-side arrangement. An operating member (13) is a pedal for a foot switch or the like and is capable of substantially simultaneously closing and opening the first switch (11) and the second switch (12) in substantially the same degree. The irradiation switch unit may further be provided with a cover (16) for covering the operating member (13). In a continuous irradiation mode or the like in which a laser beam can be emitted for a time equal to or nearly equal to a time interval in which the irradiation switch unit are operated, a laser beam can be emitted only when both the first switch (11) and the second switch (12) are turned on.

17 Claims, 3 Drawing Sheets

LASER APPARATUS

BACKGROUND OF THE INVENTION

The present invention relates to a laser apparatus and, more particularly, to an excellently safe laser apparatus for medical application which can terminate a laser irradiation without fail even if an irradiation switch unit has trouble during the irradiating operation.

Generally, by using a laser apparatus for medical application, a doctor manipulates a handpiece by hand and operates the irradiation switch unit by hand or by foot to turn on and off the laser unit for irradiating a diseased part of a patient with a laser beam. In a conventional laser apparatus with a laser unit as a light source, a push-type irradiation switch unit internally has one switch and one return spring.

SUMMARY OF THE INVENTION

If the contacts of the switch of the push-type irradiation switch unit are locked accidentally in a closed state, i.e., an on-state, during an irradiating operation in a continuous irradiation mode, the irradiating operation cannot be terminated by-operating the irradiation switch unit so as to turn off the laser unit. If the return spring of the laser irradiation switch unit breaks accidentally during an irradiating operation in the continuous irradiation mode, the switch does not open even if the irradiation switch unit is operated so as to open the switch, and the irradiating operation cannot be terminated.

Accordingly, it is an object of the present invention to provide a highly reliable laser apparatus which, even if the components of the irradiation switch unit have trouble where a continuous irradiation mode is set, is capable of terminating an irradiating operation without fail by turning off the irradiation switch unit.

According to one aspect of the present invention, provided is a laser apparatus which uses a laser as a light source, and capable of being set for a continuous irradiation mode where a laser beam is irradiated for a time equal to or nearly equal to a time interval in which an irradiation switch unit for the laser is operated, said laser apparatus comprising:

an irradiation switch unit including a first switch and a second switch electrically connected in series to each other, and an operating member capable of substantially simultaneously closing and opening the first and the second switches in substantially the same degree;

wherein the laser beam is emitted only when both the first and the second switches are closed by the operating member where the continuous irradiation mode is set.

In this invention, types and/or the number of switches included in the irradiation switch unit can be at least two. Types and the number of return springs included in the irradiation switch unit can be at least two. Since the laser apparatus is thus formed, the irradiating operation can surely be terminated by turning off the irradiation switch unit even if the component parts of the irradiation switch unit have trouble during the irradiating operation, for example, in the continuous irradiation mode.

DETAILED DESCRIPTION OF THE PREFERRED EMBODIMENTS

Figure 1:
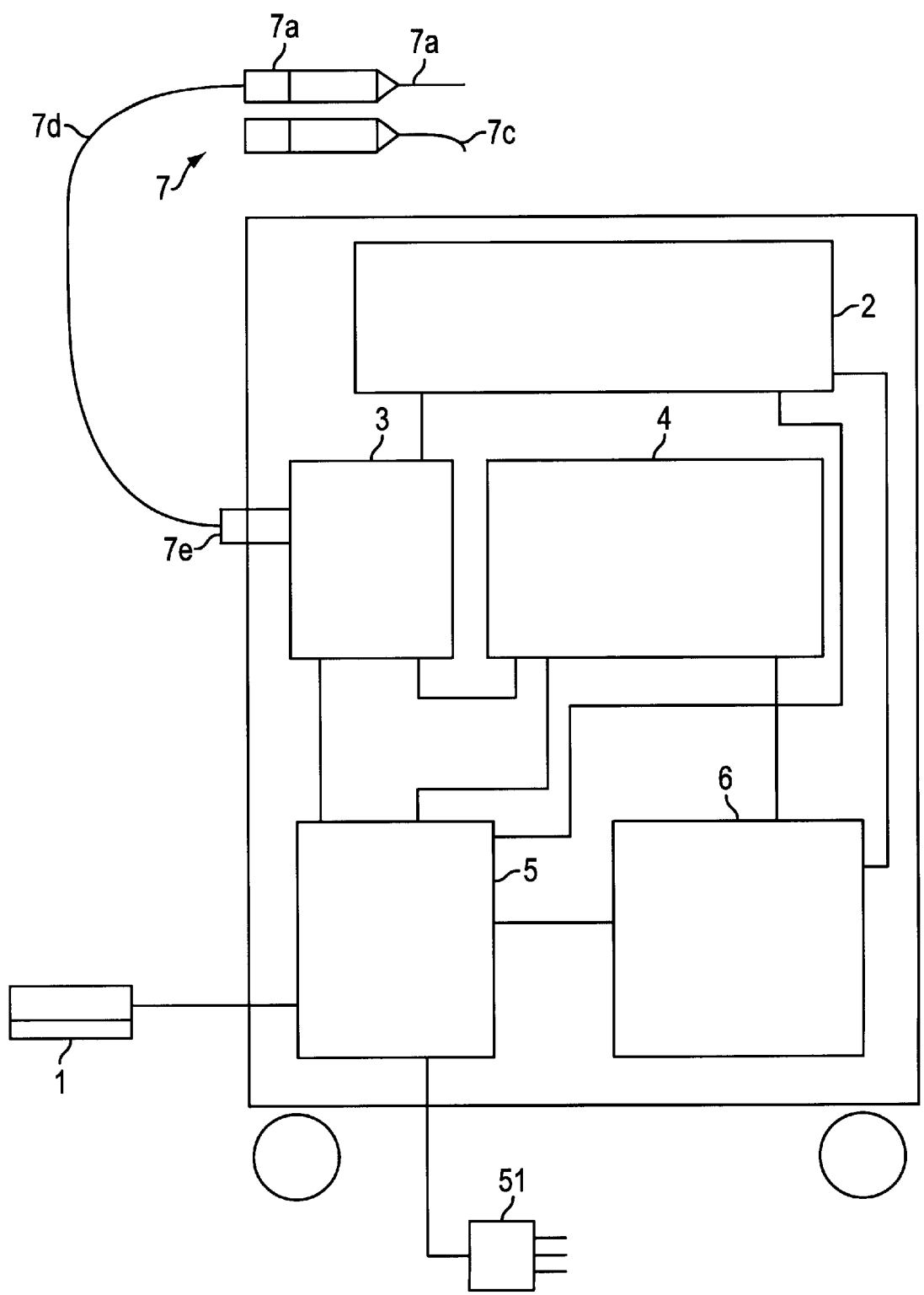
FIG. 1 is a typical view of a laser apparatus relating to the present invention.

FIG. 1 shows a typical view of a laser apparatus relating to the present invention. Referring to FIG. 1, the laser apparatus has an irradiation switch unit 1, a control panel 2, an optical unit 3, a laser head unit 4, an electrical unit 5, a cooling unit 6 and a light transmitting unit 7.

The irradiation switch unit 1 is a hand-operated switch unit or a foot-operated switch unit. The control panel 2 has components such as a control board, operating switches, an audio indication unit, a visual indication unit and a calibrating photodetecting unit. The optical unit 3 has components such as a shutter and an optical connector. The laser head unit 4 has components such as a laser rod, a laser mirror and a flash lamp. The electrical unit 5 has components such as a laser power supply, an electrical controller and a supply plug 51. The cooling unit 6 has components such as a radiator, an ion-exchange resin, a pump, a filter, a tank and sensors. The light transmitting unit 7 has components such as a handpiece body 7a, a straight-type handpiece head 7b and a curved-type handpiece head 7c. The light transmitting unit 7 is connected to the optical unit 3 by an optical fiber cable 7d and a connector 7e.

An operator, such as a doctor, holds the handpiece by hand, and operates the irradiation switch unit by hand or by foot to turn on and off laser beam emission switch included in the irradiation switch unit 1 for desired irradiation with a laser beam. A proper operating mode can be set by operation of the control panel 2. For example, a laser beam can be emitted for a time equal to or nearly equal to a time interval in which the laser beam emission switch is closed where a continuous irradiation mode is selected. In the present invention, the continuous irradiation mode includes a mode in which a laser beam is emitted in successive pulses, and a mode in which a laser beam of a proper waveform is emitted periodically in successive pulse.

Figure 2A:
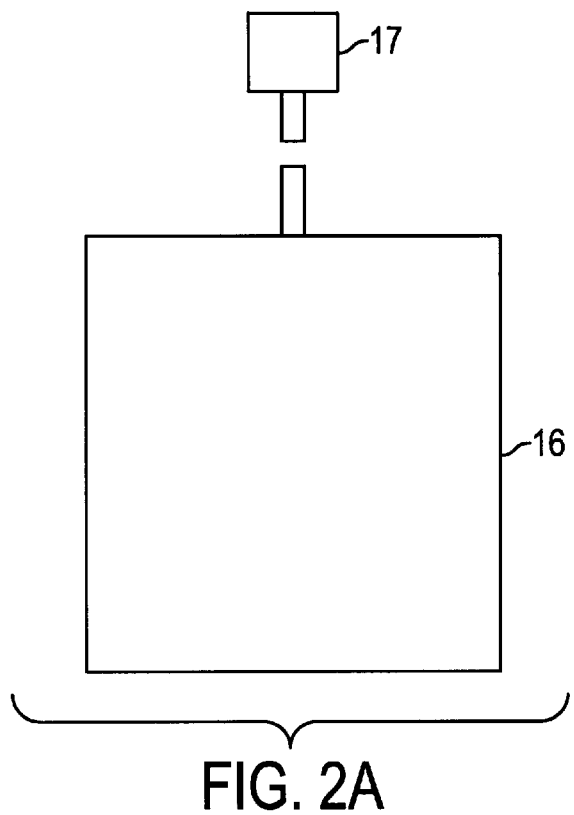
FIGS. 2A and 2B are views of an irradiation switch unit relating to the present invention.
Figure 2B:
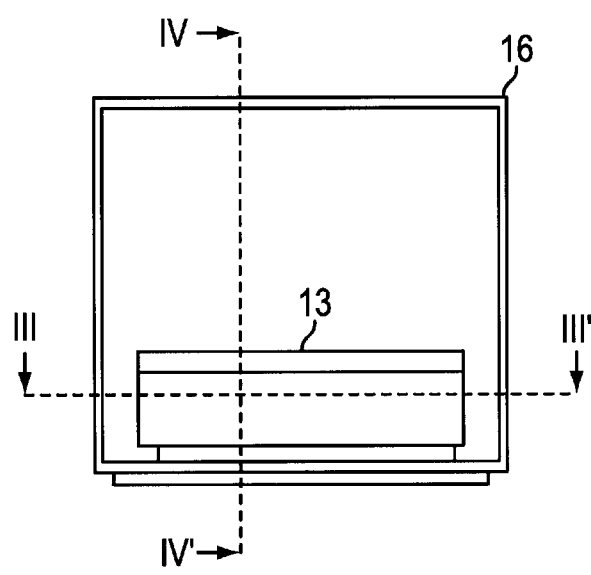

FIG. 2 shows the irradiation switch unit. This irradiation switch unit is, for example, of a foot-operated type. FIG. 2A is a top view of the irradiation switch unit, and FIG. 2B is a front view taken from the side of an opening through which the foot is inserted in the irradiation switch unit.

Figure 3:
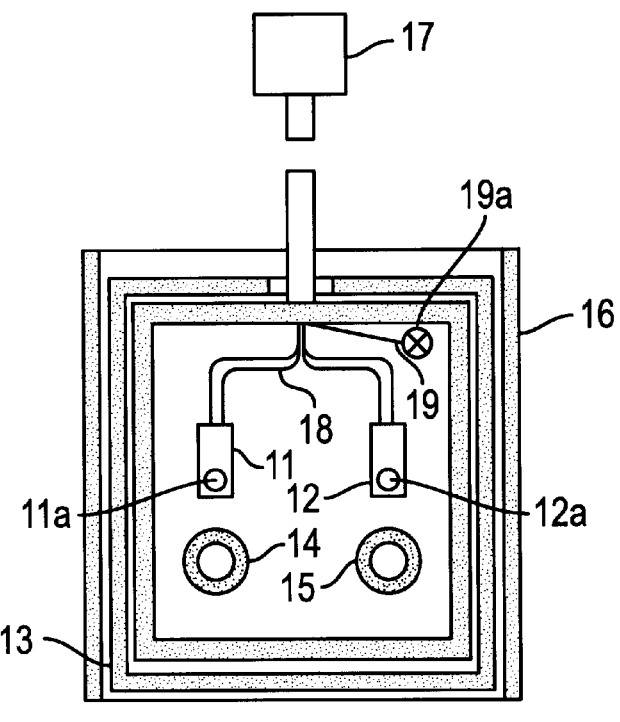
FIG. 3 is a sectional view taken on line III–III' in FIG. 2B.
Figure 4:
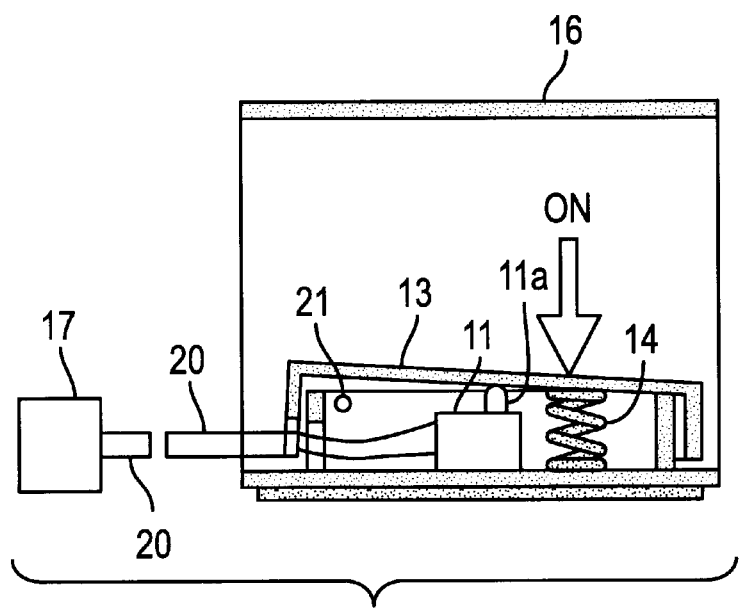
FIG. 4 is a sectional view taken on line IV–IV' in FIG. 2B.

FIG. 3 is a sectional view taken on line III–III' in FIG. 2B, and FIG. 4 is a sectional view taken on line IV–IV' in FIG. 2B.

The irradiation switch unit has a first switch 11, a second switch 12, an operating member 13, return springs 14 and 15, a cover 16, a connector plug 17, signal lines 18, a ground line 19, a cable 20 and a shaft 21.

For the first switch 11 and the second switch 12, contactless switches which do not throw off sparks in an inflammable atmosphere, such as photocouplers, or the like can be used. The switches 11 and 12 may be those of the type which are closed and opened by moving switch buttons 11a and 12a, or those of the type which are closed and opened according to the movement of a member. Its movement corresponds to the movement of the operating member 13. The switches 11 and 12 are connected electrically in series by the signal lines 18 and are disposed in a side-by-side arrangement. The operating member 13 is a push button or a pedal for a foot switch. The operating member 13 is supported for turning on a shaft 21. The operating member 13 is capable of substantially simultaneously closing and opening the first switch 11 and the second switch 12 in substantially the same degree. The irradiation switch unit 1 may further be provided with a cover 16 covering the operating member 13 to avoid accidental irradiation with a laser beam. The irradiation switch unit 1 is connected to the electrical unit 5 or the like of the laser apparatus by the connector plug 17. The ground line 19 is fastened to the operating member 13 with a ground screw 19a or the like for avoiding noise generation and malfunction.

When the laser apparatus is set for a continuous irradiation mode in which a laser beam can be projected for a time equal to or nearly equal to a time interval in which the irradiation switch unit 1 are closed, a laser beam can be emitted only in a state where both the first switch 11 and the 10 second switch 12 are closed.

The irradiation switch unit 1 may employ a switching mechanism other than the foot-operated switching mechanism, such as a finger-operated, a hand-operated or an arm-operated switching mechanism. The switching mechanism may employ optical switches such as photosensors, or electrical switches such as sensitive switches. The irradiation switch unit 1 may be provided with three or more switches instead of the two switches, i.e., the first switch 11 and the second switch 12. When the irradiation switch unit 1 is provided with a plurality of switches, the switches may be connected in series or a plurality of parallel circuits of those switches may be connected in series. The first switch 11 and the second switch 12 may be of different types, respectively.

Preferably, the irradiation switch unit 1 is provided with at least two return springs 14 and 15 to return the operating member 13 to its initial position. Even if one of the return springs should fail to function properly, the operating member 13 can be returned to its initial position by the other one. Furthermore, the irradiation switch unit 1 may be provided with return springs of at least two types. For the return springs, for example, coil springs or plate springs may be used. The irradiation switch unit 1 may be of a drip-proof type and/or a anti-water-soak type Alarm means to cope with the failure of the irradiation switch unit 1 will be described hereinafter. The alarm means is, for example, incorporated into the electrical unit 5 and/or the control panel 2 shown in FIG. 1.

For example, if either the first switch 11 or the second switch 12 has trouble and fails to close, the electrical unit 5 or the like detects the failure of the switch 11 or 12 and provides a visual alarm on the control panel 2 or provides an audio alarm. If both the first switch 11 and the second switch 12 doos not turned off when the operating member 13 is operated, the failure of the irradiation switch unit 1 is detected by the electrical unit 5 and the control panel 2, and a visual or audio alarm is give to that effect. For detecting failures, for example, failure detecting units may be incorporated into the switches 11 and 12 of the irradiation switch unit 1, respectively, and the output signals of the failure detecting units may be detected by the electrical unit 5. The laser apparatus may further be provided with a safety means capable of terminating the emission of the laser beam when a failure is detected by such an alarm means. For example, the safety means may close the shutter of the optical unit 3 or may cut off power supply from the electrical unit 5 to the laser head unit 4 for stopping the laser emission.

What is claimed is:

1. A laser apparatus which uses a laser as a light source, and capable of being set for a continuous irradiation mode where a laser beam is irradiated for a time equal to or nearly equal to a time interval in which an irradiation switch unit for the laser is operated, said laser apparatus comprising:

an irradiation switch unit including a first switch and a second switch electrically connected in series to each other, and an operating member extending over and contactable with the first and second switches, the member including a push-switch mechanism represented by a pedal for a foot switch which is stepped on and turned on, wherein the laser beam is emitted only when both the first and the second switches are closed by the operating member where the continuous irradiation mode is set.

2. The laser apparatus according to claim 1, wherein the first and the second switches are of different types, respectively.

3. The laser apparatus according to claim 1, wherein said irradiation switch unit has at least two return springs for returning the operating member to an open position.

4. The laser apparatus according to claim 3, wherein the return springs are of at least two types, respectively.

5. The laser apparatus according to claim 1, wherein said irradiation switch unit is of a drip-proof type and/or an anti-water-soak type.

6. The laser apparatus according to claim 1, wherein said irradiation switch unit has a cover for covering the operating member.

7. The laser apparatus according to claim 1, further comprising an alarm which detects a failure in which at least one of the first and the second switches fails to turn on, and provides a visual or audio indication of the failure.

8. The laser apparatus according to claim 1, further comprising an alarm which detects a failure in which both the first and the second switches fail to turn off, and provides a visual or audio indication of the failure.

9. The laser apparatus according to claim 7 further comprising a safety unit which stops emission of a laser beam upon the detection of a failure by the alarm.

10. A laser system, comprising: a laser having a continuous irradiation mode; and a switch unit electrically coupled to the laser, the switch unit comprising a first switch and a second switch electrically connected in series to each other, a moveable member extending over and disposed proximate to the first and second switches, wherein a first position of the moveable member is defined when a portion of the member simultaneously contacts the first and second switches and wherein a laser beam is emitted when the laser is in the continuous irradiation mode and both the first and the second switches are closed by the moveable member, and a push-switch mechanism configured as a pedal for a foot switch which is stepped on to place the moveable member in the first position.

11. The laser system according to claim 10, further comprising a push-button switch which is depressed to place the moveable member in the first position.

12. The laser system according to claim 10, further comprising:

first and second springs disposed in the switch unit and adjacent to the first and second switches, the first and second springs in contact with different portions of the moveable member.

13. The laser system according to claim 12, further comprising:

a shaft to provide a movement pivot for the moveable member, wherein in the first position, the first and second springs are compressed and in a second position, the springs are less compressed than in the first position.

14. The laser system according to claim 10, further comprising:

an alarm to detect a failure in which at least one of the first and the second switches fails to turn on, and to provide a visual or audio indication of the failure.

15. A laser safety method, comprising: providing an irradiation switch unit including a first and a second switch electrically connected in series to each other and coupled to a laser; providing an operating member that contacts the first and second switches in a first position; configuring a push-switch mechanism as a pedal for a foot switch which is stepped on to place the operational member in the first position; substantially simultaneously closing the first and second switches in substantially the same degree in the first position; operating the laser only when a control panel is set in a continuous irradiation mode and both switches are closed.

16. A laser safety method according to claim 15, further comprising:
    detecting a failure in which at least one of the first and the second switches fails to turn on, and providing a visual or audio indication to the failure.

17. A laser safety method according to claim 16, further comprising:
    stopping emission of a laser beam upon the detection of the failure by the alarm.

* * * * *